(12) United States Patent
Tucker et al.

(10) Patent No.: US 11,224,582 B2
(45) Date of Patent: Jan. 18, 2022

(54) AMINO ACID FORMULATIONS FOR PANCREATIC VIABILITY

(71) Applicant: Almeda Labs LLC, Kansas City, MO (US)

(72) Inventors: Stacy Tucker, Kansas City, MO (US); Sushrutha Nagaraj, Kansas City, MO (US)

(73) Assignee: Almeda Labs LLC, Kansas City, MO (US)

( * ) Notice: Subject to any disclaimer, the term of this patent is extended or adjusted under 35 U.S.C. 154(b) by 73 days.

(21) Appl. No.: 16/608,121

(22) PCT Filed: Apr. 24, 2018

(86) PCT No.: PCT/US2018/029077
§ 371 (c)(1),
(2) Date: Oct. 24, 2019

(87) PCT Pub. No.: WO2018/200477
PCT Pub. Date: Nov. 1, 2018

(65) Prior Publication Data
US 2020/0129465 A1    Apr. 30, 2020

Related U.S. Application Data

(60) Provisional application No. 62/489,757, filed on Apr. 25, 2017.

(51) Int. Cl.
*A61K 31/198* (2006.01)
*A61P 3/10* (2006.01)
*A61K 31/205* (2006.01)

(52) U.S. Cl.
CPC .......... *A61K 31/198* (2013.01); *A61K 31/205* (2013.01); *A61P 3/10* (2018.01)

(58) Field of Classification Search
None
See application file for complete search history.

(56) References Cited

U.S. PATENT DOCUMENTS

| | | | | |
|---|---|---|---|---|
| 4,279,917 A * | 7/1981 | Takami | ................. | A61K 31/195 514/400 |
| 7,879,796 B2 * | 2/2011 | Edens | ................. | A61K 31/198 514/6.8 |
| 8,067,471 B2 * | 11/2011 | Whippie | ................. | A23L 33/40 514/561 |
| 8,389,471 B2 * | 3/2013 | Edens | ................. | A61K 31/4172 514/6.8 |
| 8,648,040 B2 | 2/2014 | Edens et al. | | |
| 2004/0192751 A1 | 9/2004 | Abe et al. | | |
| 2009/0018196 A1 | 1/2009 | Bjork et al. | | |
| 2009/0076111 A1 | 3/2009 | Lee et al. | | |
| 2010/0317562 A1 | 12/2010 | Paolella et al. | | |
| 2014/0186466 A1 | 7/2014 | Patel | | |

FOREIGN PATENT DOCUMENTS

| | | |
|---|---|---|
| EP | 0354848 | 2/1990 |
| EP | 0591857 | 4/1994 |
| EP | 1752146 | 2/2007 |
| WO | 200249636 | 6/2002 |
| WO | 2002049636 | 6/2002 |
| WO | 2005039626 | 5/2005 |
| WO | 2005110394 | 11/2005 |
| WO | 2006102451 | 9/2006 |
| WO | 2007060924 | 5/2007 |

OTHER PUBLICATIONS

International Search Report and Written Opinion in corresponding PCT/US2018/029077, dated Jul. 9, 2018.
Newsholme, et al., "Amino Acid Metabolism, B-Cell Function, and Diabetes", Diabetes, vol. 55, Supplement 2, Dec. 2006.
Wikipedia, Glycated hemoglobin, Apr. 7, 2017 at https://en.wikipedia.org/w/index.php?title=Glycated_hemoglobin&oldid=774301065.
Blass, Beyond the Pancreas: Researchers Targeting Immune-System Creation Gland, Diabetes Mine, Dec. 20, 2012 available at: https://www.healthline.com/diabetesmine/beyond-the-pancreas-researchers-targeting-immune-system-creation-gland#.
Ha, et al., "Role of pancreatic L-asparagine synthetase in homeostasis of L-asparagine", Am J Physiol. Jun. 1979;236(6):E746-53 (abstract attached).
Copps, et al., "Regulation of insulin sensitivity by serine/threonine phosphorylation of insulin receptor substrate proteins IRS1 and IRS2", Diabetologia. Oct. 2012;55(10):2565-2582.
Jun, et al., "Role of glutamic acid decarboxylase in the pathogenesis of type 1 diabetes", Cell Mol Life Sci. Nov. 2002;59(11):1892-901 (abstract attached).
LiverDocotor, How Healthy Is Your Pancreas? accessed on Jan. 10, 2020, available at: https://www.liverdoctor.com/health-pancreas/.
Dawra, et al., "L-arginine-induced experimental acute pancreatitis", Division of Basic and Translational Research, Department of Surgery, University of Minnesota, Version 1.0, Mar. 8, 2012.
Adeghate, et al., "L-arginine stimulates insulin secretion from the pancreas of normal and diabetic rats" Amino Acids. 2001;21(2):205-9 (abstract attached).
Arafa, et al., "Acetyl-L-carnitine ameliorates caerulein-induced acute pancreatitis in rats", Basic Clin Pharmacol Toxicol. Jul. 2009;105(1):30-6.
Becker, et al., "Pancreas Transplantation with Histidine-Tryptophan-Ketoglutarate (HTK) Solution and University of Wisconsin (UW) Solution: Is There a Difference?", Department of General, Visceral, and Transplant Surgery, Medical School of Hannover Hannover, Germany, Feb. 22, 2007.

(Continued)

*Primary Examiner* — My-Chau T. Tran
(74) *Attorney, Agent, or Firm* — Hovey Williams LLP

(57) ABSTRACT

Amino acid formulations for pancreatic vitality. The formulations comprise a mixture of a plurality of amino acids, wherein the mixture comprises at least one amino acid selected from the group consisting of serine, glutamic acid, and/or carnitine. Methods of enhancing pancreatic vitality, stabilizing blood glucose levels, and improving A1C levels in subjects in need thereof are also described.

11 Claims, 10 Drawing Sheets

(56) References Cited

OTHER PUBLICATIONS

Lee, et al., "Histidine and carnosine delay diabetic deterioration in mice and protect human low density lipoprotein against oxidation and glycation", Eur J Pharmacol. Apr. 18, 2005;513(1-2):145-50 (abstract attached).
Arrieta-Cruz, et al., "Suppression of Endogenous Glucose Production by Isoleucine and Valine and Impact of Diet Composition", European Journal of Pharmacology, vol. 513, Issues 1-2, Apr. 18, 2005, pp. 145-150.
Al-Malki, "Suppression of acute pancreatitis by L-lysine in mice", BMC Complementary and Alternative Medicine (2015) 15:193.
Sulochana, et al., "Beneficial effect of lysine and amino acids on cataractogenesis in experimental diabetes through possible antiglycation of lens proteins", Exp Eye Res. Nov. 1998;67(5):597-601 (abstract attached).
Supplementary Search Report in corresponding European Patent Application Serial No. 18792185.3, dated Dec. 1, 2020.

* cited by examiner

AMINO ACID FORMULATIONS FOR PANCREATIC VIABILITY

CROSS-REFERENCE TO RELATED APPLICATIONS

The present application is the U.S. National Stage of International Patent Application No. PCT/US2018/029077, filed Apr. 24, 2018, which claims the priority benefit of U.S. Provisional Patent Application Ser. No. 62/489,757, filed Apr. 25, 2017, entitled AMINO ACID FORMULATIONS FOR PANCREATIC VIABILITY, each of which is incorporated by reference in its entirety herein.

BACKGROUND OF THE INVENTION

Field of the Invention

The present invention relates to synergistic amino acid formulations for enhancing pancreatic viability.

Description of Related Art

Type 2 Diabetes is a chronic condition affecting millions of people in the US. Type 2 Diabetes affects the way the body metabolizes sugar (glucose), resulting in either resisting the effects of insulin or deficient insulin production to maintain a normal glucose level. There have been several attempts to cure the disease and currently there is no single drug based/statistically validated method which can live up to the claim of curing the disease. The challenge currently the medical and healthcare providers face is controlling and stopping the disease progression.

Most prior art and medicinal approaches have been to find synthetic variants of insulin or other hypoglycemia inducing substances. However, the primary emphasis should be on enhancing the cellular health and viability. Prior art use of amino acids is limited to finding a solution for the glucose insufficiency. Even though multiple amino-acid based blends have been in the market for years, there is not a single product which is completely based on amino acids.

SUMMARY OF THE INVENTION

The present invention is broadly concerned with amino acid formulations for pancreatic vitality. In one aspect, the formulations comprise a mixture of a plurality of amino acids, wherein the mixture comprises at least one amino acid selected from the group consisting of serine, glutamic acid, and/or carnitine.

The amino acid formulations improve and enhance, pancreatic vitality in subjects in need thereof, or maintain (healthy) pancreatic vitality in healthy individuals. The formulations are useful for methods of enhancing pancreatic islet cell viability. The method generally comprises contacting a pancreatic islet cell with a therapeutically effective amount of an amino acid formulation according to the various embodiments of the invention.

In one aspect, the formulations are useful for decreasing (or stabilizing) blood glucose levels in a subject in need thereof (e.g., one having elevated blood glucose levels). This may include a diabetic or prediabetic individual, as well as a healthy individual under a heavy glucose load (e.g., after too many sweets) or simply wanting to maintain healthy pancreatic function. In general, the current recommended "normal" blood glucose levels (tested while fasting) for non-diabetic individuals should be between 70 to 100 mg/dL, and about 125 mg/dL non-fasting. For diabetic individuals, "normal" fasting blood glucose levels are between 80-130 mg/dL, and less than 189 mg/dL non-fasting. "Non-fasting" refers to glucose levels tested between 1 and 2 hours after the beginning of a meal. Thus, "elevated" levels of blood glucose include those above the thresholds noted above, depending upon the method of testing. Methods of reducing or stabilizing blood glucose levels generally comprise administering a therapeutically effective amount of the amino acid formulation to the subject in need thereof for a therapeutically effective amount of time.

In one aspect, the formulations are useful for decreasing (or stabilizing) A1C levels in a subject in need thereof. This may include a diabetic or prediabetic individual, as well as a healthy individual under a heavy glucose load (e.g., after too many sweets) or simply wanting to maintain healthy pancreatic function. In general, the current recommended "normal" A1C level is below 5.7% for non-diabetic individuals. Diabetic individuals typically present with A1C levels of 6.5% or over. Prediabetic individuals typically present with A1C levels between 5.7-6.4%. Thus, "elevated" A1C levels include those above the thresholds noted for a given individual. Methods of reducing or stabilizing A1C levels generally comprise administering a therapeutically effective amount of the amino acid formulation to the subject in need thereof for a therapeutically effective amount of time.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
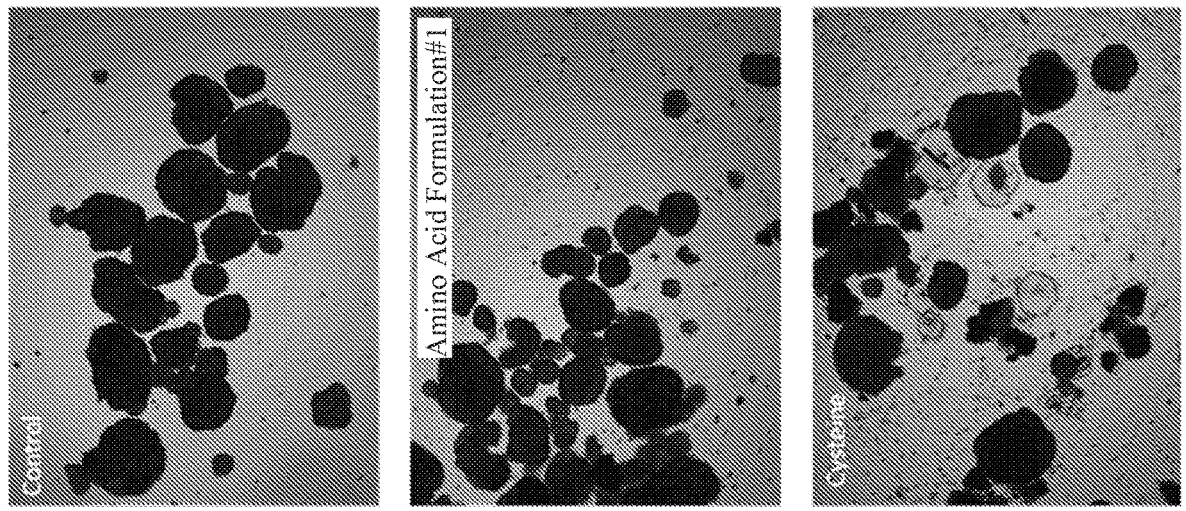
FIG. 1 shows sample images of islets from each condition stained with Dithizone illustrating their islet identity.

The present invention is concerned with amino acid formulations for pancreatic vitality. The amino acid formulations reduce oxidative stress and inflammatory responses. Thus, mitigating not only the insulin secretion problem but enhancing vitality of pancreatic cells. The individual amino acids are combined in synergistic blends according to the embodiments of the invention. The amino acid formulations are particularly useful for improving pancreatic vitality in subjects with impaired glucose metabolism, as well as diabetes.

In one or more embodiments, an amino acid formulation is provided which comprises (consists or consists essentially of) a mixture of amino acids. In one or more embodiments, the amino acids are selected from at least one of serine, glutamic acid, and/or carnitine. In one or more embodiments, amino acid formulations according to the invention comprise at least serine and glutamic acid. In one or more embodiments, amino acid formulations comprise at least carnitine. In one or more embodiments, amino acid formulations according to the invention further comprise isoleucine and/or lysine (preferably L-lysine HCl). In one or more embodiments, amino acid formulations consist of a mixture of amino acids, wherein the amino acids are further selected from one or more of asparagine, cysteine, arginine, and/or histidine. The mixture of amino acids comprises at least two different amino acids, preferably at least 3 different amino acids, more preferably at least 4 different amino acids, even more preferably, at least 5 different amino acids, and most preferably 5 different amino acids blended together in a unit dosage formulation. In one or more embodiments, the mixture consists or consists essentially of 5 different amino acids blended together in unit dosage form.

In one or more embodiments, a first amino acid formulation is provided, which consists essentially (or even consists) of a mixture of threonine, asparagine, serine, glutamic acid, and optionally cysteine. A second amino acid formulation is provided which consists essentially (or even consists) of a mixture of arginine, carnitine, histidine, isoleucine, and lysine. A third amino acid formulation is provided which consists essentially (or even consists) of serine, threonine, glutamic acid, isoleucine, and lysine. A fourth amino acid formulation is provided which consists essentially (or even consists) of serine, carnitine, glutamic acid, isoleucine, and lysine. As used herein, the phrase "consisting essentially" or "consists essentially" of means that the formulations are preferably limited to the specified ingredients, but allow for the inclusion of minor impurities, additives, fillers, etc. that do not materially affect the basic characteristics of the formulation.

Regardless of the embodiment, the amino acids are preferably blended in an about 1:1 weight ratio or about 1:1.2 weight ratio for some amino acids (e.g., those provided in salt form, such as lysine to ensure the amount of available amino acid is about 1:1). Exemplary formulations are essentially free (i.e., less than 1%) of any other additives, active agents and/or impurities, it being appreciated that minor amounts of impurities may be present due to amino acid manufacturing processes. For example, the formulations are preferably essentially free of preservatives, colorants, sweeteners, other nutrients (vitamins or minerals), and the like. In any case, pharmaceutical grade amino acids (i.e., 99% pure, discrete amino acids not conjugated to other proteins) are preferably used, including functionalized (e.g., esterified or acylated) forms and salts (e.g., HCl, acetates, sulfates, glutamates, etc.) thereof. As noted above, it will be appreciated that when functionalized or salt forms are used in a blend, the amount used may be adjusted (increased) to ensure that the total amount of available amino acid (active) is maintained. It will also be appreciated that amino acids used in the invention are L-form amino acids, whether or not expressly specified in referring to the particular amino acid.

In one or more embodiments, the mixture is substantially free of and comprises less than 5% by weight, preferably less than 1% by weight, an even more preferably less than 0.5% by weight of one or more (and in some cases all of) amino acids selected from the group consisting of: alanine, aspartic acid, glutamine, glycine, leucine, methionine, phenylalanine, proline, tryptophan, tyrosine, and valine. In other words, such amino acids are not intentionally added, and are preferably excluded in the inventive formulations. In addition, although cysteine and asparagine can be used in certain formulations, in other embodiments, the formulation is substantially free of and comprises less than 5% by weight, preferably less than 1% by weight, an even more preferably less than 0.5% by weight of either of cysteine or asparagine. In other words, cysteine and asparagine are preferably excluded in certain embodiments. In one or more embodiments, the formulation is substantially free of and comprises less than 5% by weight, preferably less than 1% by weight, an even more preferably less than 0.5% by weight of arginine and/or histidine. In other words, arginine and histidine are preferably excluded in certain embodiments.

Preferably, the amino acid formulation is provided as a unit dosage form, particularly suitable for oral administration. The unit dosage form can be from about 400-600 mg, preferably from about 500-600 mg, more preferably from about 500-550 mg, and even more preferably about 500-520 mg (where the term "about" refers to +/−5 mg from the indicated amount). In one or more embodiments, the formulation is suitable for a total daily dosage form of from about 0.5 grams to about 2 grams per day, preferably from about 0.6 grams to about 1.5 grams per day, and more preferably from about from about 1 grams to about 1.5 grams per day (where the term "about" refers to +/−0.2 grams from the indicated amount). In certain embodiments, the amino acid formulation is provided in an oral supplement, which can be selected from the group consisting of pill, tablet, capsule, liquid solution, gel cap, and the like. In certain embodiments, the amino acids are in powder form and encapsulated in a vegetable capsule. Extended release capsules may also be used. It is also contemplated that the amino acid formulations can be provided as part of a nutritional product, such as snack or meal replacement bars, powders, smoothies, shakes, juices, gels, and the like. Regardless, the low-dosage combination of the four or five amino acid blends produces a rather unique synergistic modulation which translates into greater pancreatic vitality.

In one or more embodiments, a therapeutically effective amount of the amino acid formulation is administered to a subject in need thereof for a therapeutically effective amount of time. Such individuals include those suffering from a condition or disease affecting pancreatic vitality and/or islet cell function such as Type-2 Diabetes, Pancreatic exocrine insufficiency, and prediabetic insulin insufficiency, resulting in impaired glucose metabolism. As used herein, the term "therapeutically effective" refers to the amount and/or time period that will elicit the biological or medical response of a tissue, system, animal, or human that is being sought by a researcher or clinician, and in particular elicit some desired therapeutic effect. For example, in one or more embodiments, therapeutically effective amounts and time periods are those that enhance, improve, maintain pancreatic islet cell functioning and vitality (resulting in improved blood glucose levels, A1C levels, pancreatic islet cell viability, and the like). One of skill in the art recognizes that an amount or time period may be considered "therapeutically effective" even if the condition is not totally eradicated but improved partially. Exemplary dosages range from about 0.5 grams to about 2 grams over a 24-hr period, preferably from about 0.6 grams to about 1.5 grams, and more preferably from about from about 1 grams to about 1.5 grams (where the term "about" refers to +/−0.2 grams from the indicated amount). Dosages can be repeated daily for a period of about 20 to about 40 weeks, or taken daily on an ongoing basis as needed or as desired.

The amino acid formulation reduces oxidative stress, decreases inflammation, and increases pancreatic vitality. Pancreatic vitality is exemplified by increased efficiency of pancreatic islets, increased islet metabolism, and increased insulin production levels (in previously insulin-deficient individuals). The amino acid formulations also increase islet viability.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

1. Introduction

The objective of the experiment was to test the effect of long-term exposure of rat islets to Amino Acid Formulation #1 and compare those results to the currently-marketed amino acid, cysteine. A group without added amino acids was used as a control group. The comparison was based on the number of dead cells within islets over time, a count of the number of islets surviving over time, and the functional test of cellular metabolism after long-term exposure.

Freshly-dispersed rat islets were chronically exposed to high glucose conditions (11.6 mM glucose which is equivalent to approximately 210 mg/dl blood glucose for humans) in order to mimic a diabetic condition. During the long-term (11 day) exposure, the islets were administered Amino Acid Formulation #1 or cysteine (at the same concentration) or culture media with no added amino acids. Islets exposed to Amino Acid Formulation #1 had higher viability, improved survival compared to the cysteine group, and higher metabolism compared to controls.

Exposure over the same time period to cysteine alone was correlated with necrotic and apoptotic cell death and poor survival than either of the other 2 groups.

Rat islets were isolated from the pancreata of female animals under approved protocol and SOPs. The islets were maintained in an incubator at 37° C. and 5% $CO_2$ for the duration of the study. All work was done under a biosafety hood to ensure sterility of the cultures. The Biotek Cytation 5 plate reader was utilized to measure the viability and metabolism values of each tested group as well as the corresponding negative control samples, to ensure each sample tested had achieved optimal loading. The imaging capabilities of the Cytation plate reader was utilized for survival values.

2. Materials & Methods 2.1 Sample Preparation

Isolated rat islets were cultured in 100 $cm^2$ cell culture plates (untreated) in 20 ml of Roswell Park Memorial Institute (RPMI) media. 24 hours following isolation, the baseline viability and survival readings were taken. Islets were removed from the dish and placed in 50 ml tubes. Islets were allowed time to settle to the bottom of the tube. The excess media was removed, and the islets were moved to microcentrifuge tubes, and DPBS solution was added to each tube. Cells were washed and fresh DPBS added.

Islets had media changed every 2 days with continuous exposure to Amino Acid Formulation #1, Cysteine alone, or media alone. Amino Acid Formulation #1 was prepared in the lab using amino acid capsules:

TABLE 1

Summary of Amino Acid Formulation #1

| Capsule ID | Capsule Weight (g) | White Powder Removed (g) |
|---|---|---|
| Threonine | 0.56 | 1.99 |
| | 0.57 | |
| | 0.61 | |
| | 0.59 | |
| L-Serine | 0.58 | 2.12 |
| | 0.60 | |
| | 0.67 | |
| | 0.61 | |
| Asparagine | 0.59 | 2.08 |
| | 0.58 | |
| | 0.61 | |
| | 0.59 | |
| Glutamic Acid | 0.60 | 2.06 |
| | 0.60 | |
| | 0.60 | |
| | 0.61 | |
| L-Cysteine | 0.75 | 2.62 |
| | 0.77 | |
| | 0.77 | |
| | 0.51 | |

In order to keep the ratio of the components identical, this blend was used for all studies for Amino Acid Formulation #1.

The industry comparison contained cysteine alone. The following capsules were used to create the comparison treatment.

TABLE 2

Industry Comparison

| Capsule ID | Capsule Weight (g) | Powder Removed (g) |
|---|---|---|
| Cysteine | 0.79 | 5.18 |
| | 0.73 | |
| | 0.74 | |
| | 0.77 | |
| | 0.77 | |
| | 0.76 | |
| | 0.76 | |
| | 0.76 | |

The test articles were added to RPMI media for cell maintenance. RPMI media is one of 2 commonly used for islet cell culture. It was chosen because it has the lowest level of added amino acids, and it contains 11.6 mM glucose, which mimics a diabetic condition of 210 mg/dl blood glucose.

TABLE 3

RPMI Media Amino Acids

| Amino Acid | Concentration g/L |
|---|---|
| L-Alanyl-L-Glutamine | ND |
| L-Arginine | 0.2 |
| L-Asparagine (anhydrous) | 0.05 |
| L-Aspartic Acid | 0.02 |
| L-Cysteine | 0.0652 |
| L-Glutamic Acid | 0.02 |
| L-Glutamine | ND |

TABLE 3-continued

RPMI Media Amino Acids

| Amino Acid | Concentration g/L |
|---|---|
| Glycine | 0.01 |
| L-Histidine | 0.015 |
| Hydroxy-L-Proline | 0.02 |
| L-Isoleucine | 0.05 |
| L-Leucine | 0.05 |
| L-Lysine | 0.04 |
| L-Methionine | 0.015 |
| L-Phenylalanine | 0.015 |
| L-Proline | 0.02 |
| L-Serine | 0.03 |
| L-Threonine | 0.02 |
| L-Tryptophan | 0.005 |
| L-Tyrosine | 0.02883 |
| L-Valine | 0.02 |

ND = Not Detected.

The working solutions contained 1 g/1 L concentration of Amino Acid Formulation #1 or cysteine alone prepared in RPMI.

After mixing, particulates were noted in the solutions, but were no longer noticeable after 2 hours at 37° C. The working medium was kept at 37° C. in incubator with islets.

2.2 Assay Execution 2.2.1 Viability Assay 24 hours following isolation, the baseline viability and survival readings were taken. 25-50 islets were removed from the dishes and placed in 50 ml tubes. Islets were allowed time to settle to the bottom of the tube. The excess media was removed, and the islets were moved to microcentrifuge tubes, and DPBS solution was added to each tube. Cells were washed and fresh DPBS added. Propidium iodide and yo-pro were added to the tubes at a ratio of 1 µl reagent to 1 ml cells in DPBS.

Individual wells of 96-well plates were manually loaded with 10-15 islets each and checked visually under a microscope for consistency between wells. 30 minutes later, the plates were loaded into the BioTeck plate reader with readings for Yo-Pro and Propidium iodide with additional verification of islet tissue using dithizone staining.

Results were saved as images for later cellular analysis.

2.2.2 Metabolic Assay

After 11 days of continual exposure to the test compositions, metabolic activity was measured using the fluorophore, PrestoBlue. 25-50 islets were removed from the dishes and placed in 50 ml tubes. Islets were allowed time to settle to the bottom of the tube. The excess media was removed, and the islets were moved to microcentrifuge tubes, and DPBS solution was added to each tube. Cells were washed and fresh DPBS added. Presto Blue added to the tubes at a ratio of 1 µl reagent to 1 ml cells in DPBS.

Individual wells of 96-well plates were manually loaded with all remaining islets and checked visually under a microscope for consistency between wells. At 1, 2 and 6 hours following the PrestoBlue addition, the plates were loaded into the BioTeck plate reader with excitation at 485 and emission at 560 nm wavelengths with normalization to control islets.

3. Results 3.1.1 Dithizone Staining

Islets were exposed to a single dose of Amino Acid Formulation #1 or cysteine for 11 days. FIG. 1 illustrates images of islets from each condition on day 1, stained with dithizone, which identifies islet cells via dark red color.

Ample islets were isolated from each group and all stained red, indicating that they were islets. Interesting, even after 24 hours at 37° C., the cysteine still had microscopic crystals that had not gone completely into solution, as can be seen in the bottom panel.

From light microscopy, the following general observations were made: In Amino Acid Formulation #1, the islets appeared healthy, clean and without core cell death. In the control media, the same was found. Both Amino Acid Formulation #1 and the control samples had a few single cells. More single cells were noted in the cysteine condition, along with the cysteine crystals. In addition, core cell death was noted in approximately 30% of islets.

3.1.2 Apoptosis and Necrosis Staining

Figure 2:
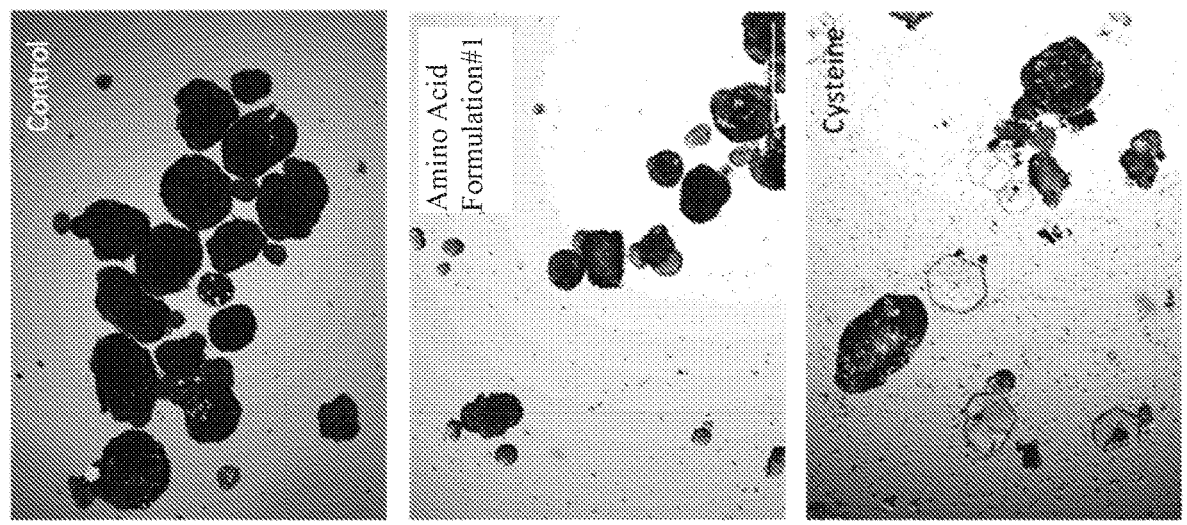
FIG. 2 shows representative images of islet day 1 viability, and staining of dead cells (4× magnification)

Staining with the cell death fluorophores, Yo-Pro and Propidium Iodide demonstrated few dead cells in the control group. Within the control islets, cell death mainly occurred via necrosis (as shown by red cells in FIG. 2). The same was true for islets exposed to Amino Acid Formulation #1 for 24 hours. Cell death in the cysteine-exposed group was greater than the other 2 and occurred through both apoptosis and necrosis. The red staining indicates cells that died due to necrosis. The green indicates cells that died due to apoptosis, and gray (lacking color) indicates live cells.

Figure 3:
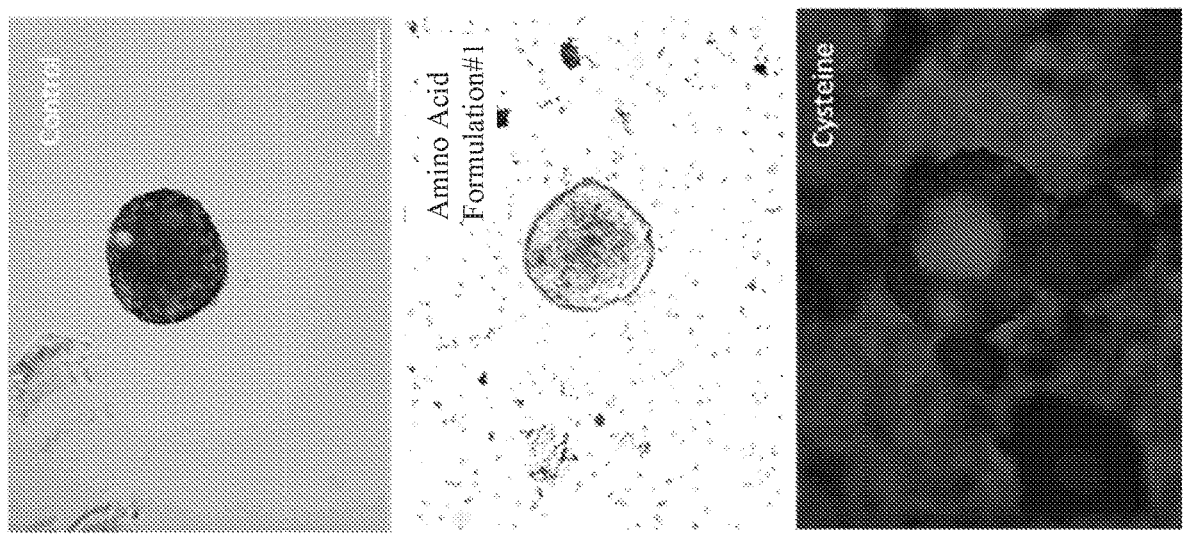
FIG. 3 shows representative images of islet day 8 viability based upon staining of dead cells after exposure to the test articles and controls (10× magnification)

The average fluorescence measurements were captured using the BioTek plate reading capabilities. The same measurements were taken on days 4 and 8. FIG. 3 illustrates examples of the islets on day 8 using 10× magnification. An example of core cell death (necrotic center) is shown in the cysteine example.

Table 4 summarizes the findings for all 3 test dates. All islets identified in each condition were scored for the percent area of apoptotic and necrotic cells. The remaining percentage was calculated as live cells. The number of islets analyzed for each group varied due to the poor survival of islets in culture over time but ranged from 8-50/group. No islets could be identified on day 8 in the cysteine group.

TABLE 4

Viability Results

| Condition | Time Point | Apoptotic Cells (%) | Necrotic Cells (%) | Live Cells (%) |
|---|---|---|---|---|
| Amino Acid Formulation #1 | Day 1 | 3.8 + 5.1 | 9.8 + 8.2 | 86.2 + 10.3 |
| | Day 4 | 0.2 + 0.5 | 2.1 + 2.3 | 97.8 + 2.6 |
| | Day 8 | 0.5 + 1.9 | 10.9 + 9.5 | 88.6 + 10.6 |
| Cysteine | Day 1 | 18.2 + 21.3 | 23.4 + 20.4 | 58.4 + 33.4 * |
| | Day 4 | 47.1 + 35.9 | 10.9 + 13.4 | 42.0 + 39.8 * |
| | Day 8 | na | na | na |
| Control | Day 1 | 8.6 + 16.8 | 11.9 + 16.7 | 79.5 + 25.0 |
| | Day 4 | 9.8 + 19.7 | 14.3 + 12.8 | 76.0 + 26.9 |
| | Day 8 | 3.6 + 5.9 | 11.6 + 10.5 | 84.8 + 12.0 | na indicates no islets could be identified in the samples.
* indicates a statistical difference from the other 2 groups, $p < 0.05$ 3.1.3 Islet Survival All groups began with the same number of total islets per group. Within 24 hours of exposure, the control and cysteine groups had 78% of the number of islets as the Amino Acid Formulation #1 group. By day 8, the control group contained 48% the number of islets compared to the Amino Acid Formulation #1 group, and no live islets could be found in the cysteine group.

3.1.4 Islet Metabolism

Metabolism of cells indicates the health of the cell. The assay used here measures metabolism by accepting electrons from newly formed NDPH, FADH, NADH and cytochromes. The more electrons accepted, the greater the molecular fluorescence. Table 5 summarizes the raw data for the metabolism studies conducted on Day 11 of incubation with the test article, and the normalized data. Data were normalized by subtracting the background fluorescence (from the blank) and dividing by the number of islets per well. At 30 minutes, the metabolism of the islets in Amino Acid Formulation #1 was 6 times greater than the control islets. When normalized for islet numbers and background signal, the islets incubated in Amino Acid Formulation #1 continued to demonstrate higher metabolism.

3.2 Summary of Data

Islet cells are difficult to maintain in culture. They do not proliferate and are not self-renewing. In fact, they are one of the most sensitive cells to inflammation in the body. For this study, islets were cultured in a high glucose environment to further stress the cells and to simulate a diabetic condition.

First, tissue from the animals was confirmed as islets through dithizone staining. Next islets were stained at days 1, 4, and 8 for viability by measuring cells undergoing apoptosis (programmed cell death) and necrotic cell death. The remaining, unstained cells were assumed to be alive. Cells exposed to Amino Acid Formulation #1 had the highest viability at each time point. However, cells exposed to cysteine had a significantly lower viability than the other two groups. In the control and Amino Acid Formulation #1 groups, more cells died of necrosis than apoptosis. Accordingly, the islets exposed to Amino Acid Formulation #1 survived 11 days in culture at higher numbers than the other groups. No islets from the cysteine group survived past 6 days in culture. Additionally, there was only 48% of the number of islets in the control group compared to the Amino Acid Formulation #1 group by day 8.

Metabolism of cells indicates their general health and activity. Metabolism of the islets in each group was measured on day 11. 30 minutes after the addition of the electron detector, the metabolism of the islets in the Amino Acid Formulation #1 group was higher than the controls and this trend continued through the 6-hour study. Knowing that there were more islets left in the Amino Acid Formulation #1 group, the data was normalized to the number of islets in each group. The normalized metabolism data are plotted in FIG. 4. With normalization, the islets in the Amino Acid Formulation #1 group were still more metabolically active.

TABLE 5

Metabolism Results

| | Raw Data | | | | Normalized Data (normalized to islet number) | | | |
|---|---|---|---|---|---|---|---|---|
| | 30 min | 1 hour | 2 hour | 6 hour | 30 min | 1 hour | 2 hour | 6 hour |
| Blank | 0.116 | 8 | 7 | 6 | na | na | na | na |
| | 0.542 | 11 | 9 | 5 | | | | |
| | 0.099 | 6 | 4 | 4 | | | | |

TABLE 5-continued

Metabolism Results

| | Raw Data | | | | Normalized Data (normalized to islet number) | | | |
|---|---|---|---|---|---|---|---|---|
| | 30 min | 1 hour | 2 hour | 6 hour | 30 min | 1 hour | 2 hour | 6 hour |
| Amino Acid Formulation #1 | 26,153 | 55,692 | 138,321 | 134,073 | 1453 | 3094 | 7685 | 7448 |
| | 33,598 | 69,895 | 139,101 | 122,917 | 1867 | 3883 | 7728 | 6829 |
| | 28,611 | 60,756 | 160,509 | 157,330 | 1590 | 3375 | 8917 | 8741 |
| Control | 6449 | 6891 | 9885 | 14.126 | 818 | 861 | 1235 | 1765 |
| | 3871 | 4341 | 7723 | 12.267 | 483 | 542 | 965 | 1533 |
| | 4268 | 4590 | 7274 | 11.863 | 533 | 573 | 909 | 1482 |

Figure 4:
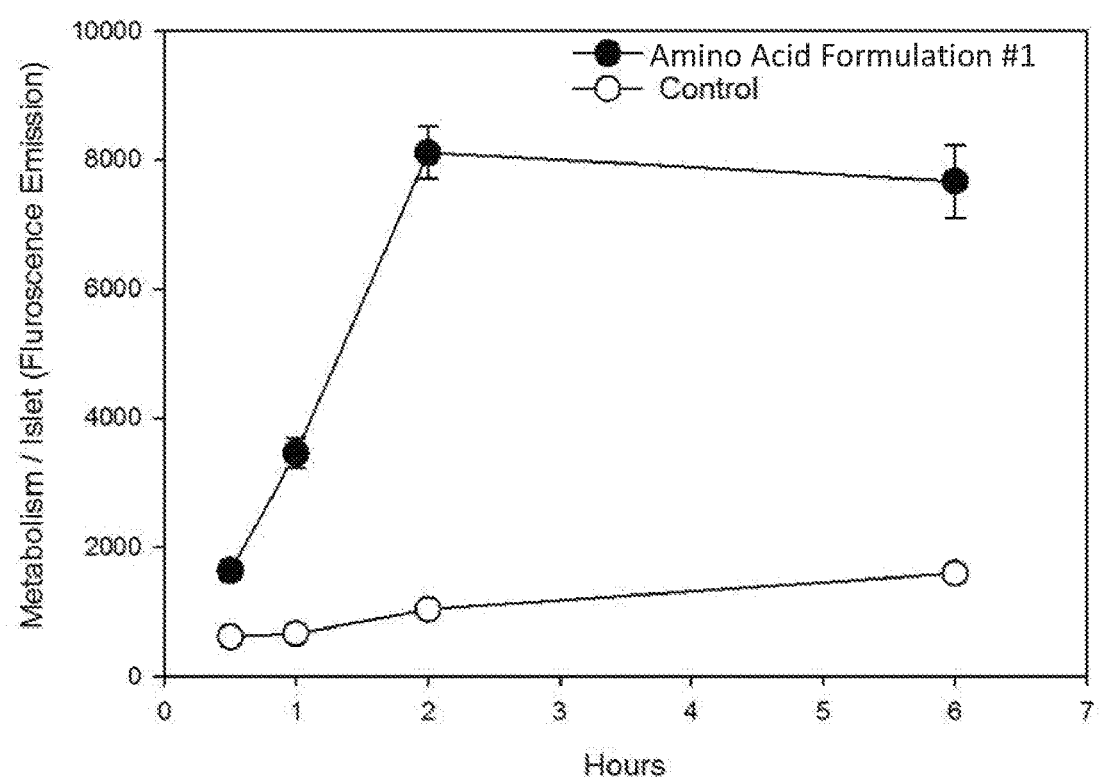
FIG. 4 is a graph of islet metabolism of islets exposed the amino acid formulation #1 and controls.

As shown in FIG. 4, 30 minutes after the addition of the metabolism detector, the metabolic level was greater in the islets from the Amino Acid Formulation #1 group (filled circles). This continued through the termination of the study.

The metabolic level of the islets in the Amino Acid Formulation #1 group was greater than the control islets at 30 minutes following the addition of the metabolism detector. This trend continued with a steep increase in the electrons accepted from the electron transport pathway in the Amino Acid Formulation #1 group and a lower slope in the controls. At 2 hours into the assay the maximum level of metabolism was detected, and it plateaued at 6 hours, while the control cells continued a low level of metabolism.

Example 2

1. Introduction

The objective of the experiment was to test the effect of long-term exposure of canine islets to the Amino Acid Formulation #2 at three different concentrations along with a control (0 Test Agent) group. The comparison was based on the number of dead cells within islets over time, and the functional test of cellular metabolism after long-term exposure (8 day).

Freshly-dispensed canine islets were chronically exposed to high glucose conditions (11.6 mM glucose which is equivalent to approximately 210 mg/dl blood glucose for humans), in order to mimic a diabetic condition. During the long-term (8 day) exposure, the islets were administered the Amino Acid Formulation #2 or culture media with no added amino acids. Islets exposed to the Amino Acid Formulation #2 had a statistically higher viability at the highest concentration on day 8. In addition, the islets exposed to Amino Acid Formulation #2 at the highest concentration registered higher metabolism compared to controls.

Canine islets were isolated from the pancreata of deceased donors under the Likarda approved protocol. The islets were maintained in an incubator at 37° C. and 5% CO2 for the duration of the study. All work was done under a biosafety hood to ensure sterility of the cultures. The Biotek Cytation 5 plate reader was utilized to measure the viability and metabolism values of each tested group as well as the corresponding negative control samples, to ensure each sample tested had achieved optimal loading.

2. Materials and Methods 2.1 Sample Preparation

Isolated canine islets were cultured in 100 cm$^2$ cell culture plates (untreated) in 20 ml of RPMI media. RPMI media was removed from the dishes every other day and replaced with fresh media.

Amino Acid Formulation #2 was prepared in the lab using amino acid capsules, and the measurements provided in Table 6.

TABLE 6

Formulation of Amino Acid Formulation #2 (Batch 001)

| Component | Manufacturer | Batch Number | Added weight (g) |
|---|---|---|---|
| L-Carnitine | JoMar Labs | 179025 | 5.0038 |
| L-Histidine | JoMar Labs | 220633 | 4.9990 |
| L-Arginine | JoMar Labs | 224929 | 4.9991 |
| L-Isoleucine | JoMar Labs | 212435 | 4.9955 |
| L-Lysine | JoMar Labs | 218627 | 5.0009 |

When L-Carnitine was first opened, it was noted to have large clumps of powder that were manually broken up using a pestle and mortar. After blending the components, the final product was again manually ground with a pestle and mortar to create a fine powder before dissolving.

Batch 001 was used for all studies described in this report. This blend was stored in an opaque bottle, labeled and dated.

Different solvents for dissolution of the Amino Acid Formulation #2 were tested, and the results summarized in Table 7.

TABLE 7

Dissolution Testing of Amino Acid Formulation #2 (Batch 001)

| Solvent | Methods | Results |
|---|---|---|
| RPMI media + L-Glutamine | 10 mg of Blend#2* added to 10 mL of RPMI, heated at 37° C. for 30 minutes. | Particulates noted in media after mixing. Particulates still present after 15 minutes of heating. Particulates still present after a total of 30 minutes of heating. |
| Dimethyl sulfoxide (DMSO) | 1000 mg of Blend#2* added to 1.0 mL of DMSO. After mixing, diluted in 9.0 mL RPMI | No particulates noted with the naked eye in the final product. |

*Amino Acid Formulation #2 (Batch 001)

Following the dissolution experiments, a 50 mL bottle of stock Amino Acid Formulation #2 was made at concentration of 1 mg/mL using DMSO as the solvent and as per the methods described in Table 7 with a 1:100 mixture of Amino Acid Formulation #2 stock solution and RPMI.

2.2 Assay Execution 2.2.1 Viability Assay

Canine islets were obtained from deceased donors according to Harrington et al. (Harrington S, Williams, S J, Otte, V, Barchman, S, Jones, C, Ramachandran, K, Stehno-Bittel, L. (2017) Increased efficiency of canine islet isolation from deceased donors. BMC Vet Res. In press.). Prior to exposure to the test agent, the cells were maintained in RPMI media, which was changed every 2 days as described previously.

Islets were manually placed into dishes containing fresh RPMI with control (0) 1.0, 0.5, or 0.25 mg/mL Amino Acid Formulation #2. Islets were maintained in the selective concentration of the blend throughout the 8-day study.

Approximately 30-50 islets were manually removed from the tissue culture dishes and placed in 50 ml tubes. The number of islets per dish was estimated at the end of the study by microscopically counting islets/well. Islets were allowed time to settle to the bottom of the tube. The excess media was removed, and the islets were moved to microcentrifuge tubes, and DPBS solution was added to each tube. Cells were washed and fresh DPBS added. Propidium iodide and Hoechst fluorophores were added to the tubes at a ratio of 1 µl reagent to 1 mL cells in DPBS. Hoechst binds to DNA and stains all cells (dead or alive). In contrast propidium iodide only stains dead cells.

Individual wells of 96-well plates were manually loaded with approximately 5 islets each and checked visually under a microscope for consistency between wells. 30 minutes later, the plates were loaded into the BioTeck plate reader for imaging of the live-dead fluorophores. Images were saved for later analysis.

Images were analyzed using Photoshop Software (Adobe) by counting live cells stained with Hoechst (blue) and dead cells stained with propidium iodide (red). The live cell number was divided by the total cell count in each islet section resulting in a % live value. All viability numbers expressed are an average±standard deviation of the % live values.

2.2.2 Metabolic Assay

After 8 days of continual exposure to the test articles, metabolic activity was measured using the fluorophore, PrestoBlue. 25-50 islets were removed from the dishes and placed in 50 ml tubes. Islets were allowed time to settle to the bottom of the tube. The excess media was removed, and the islets were moved to microcentrifuge tubes, and DPBS solution was added to each tube. Cells were washed and fresh DPBS added. Presto Blue added to the tubes at a ratio of 1 µl reagent to 1 ml cells in DPBS.

Individual wells of 96-well plates were manually loaded with all remaining islets and checked visually under a microscope for consistency between wells. At 0.5, 1, 3 and 7 hours following the PrestoBlue addition, the plates were loaded into the BioTeck plate reader with excitation at 485 nm and emission at 560 nm wavelengths. Raw data were saved as Excel spreadsheets and later analyzed by subtracting background values (wells with DPBS only) and normalizing to islet number/well or to the starting emission value (at time 30 minutes).

3. Results 3.1 Data & Analysis 3.1.1 Islet Morphology

Figure 5:
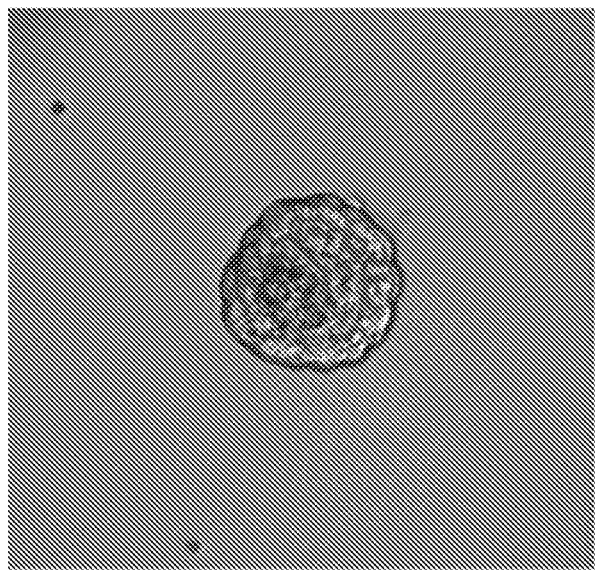
FIG. 5 is a representative image illustrating the morphology of a healthy islet incubated in 1.0 mg/mL Amino Acid Formulation #2 for 8 days, showing a smooth surface with only live (blue) cells.

Islets were exposed to three different concentrations of Amino Acid Formulation #2 for 8 days. FIG. 5 illustrates an image of an islet after 8 days of exposure to 1.0 mg/mL Amino Acid Formulation #2. The islet has a smooth surface and is stained with only live cells (Hoechst, blue). Few single dead cells, which can sometimes slough off the surface of an islet, were noted in all of the tested groups. Ample islets were isolated from each concentration to conduct all studies.

3.1.2 Viability

Figure 6:
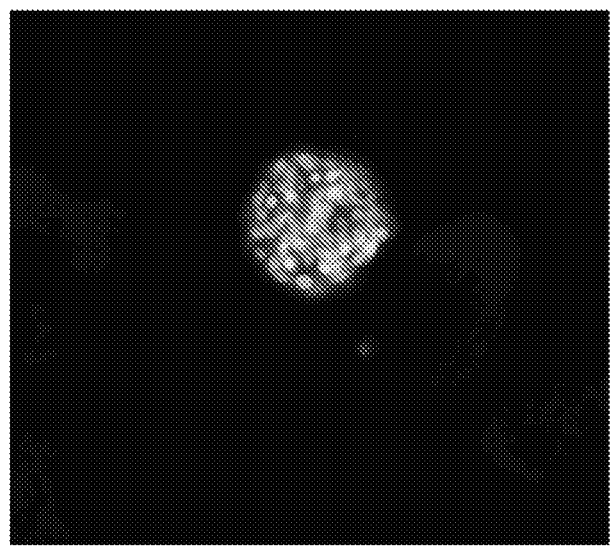
FIG. 6 is a representative image illustrating the morphology of an islet from the control group exhibiting core cell death where dead cells (PI, red cells) are found throughout the sphere, but are concentrated in the core.

Staining with the cell death fluorophores, Hoechst and propidium iodide, demonstrated few dead cells in the control group initially. When cell death occurred within the control islets, dead cells were seen scattered throughout the islet, but mainly was noted in the core (as shown by red cells in FIG. 6) and occurred through necrosis.

Figure 7:
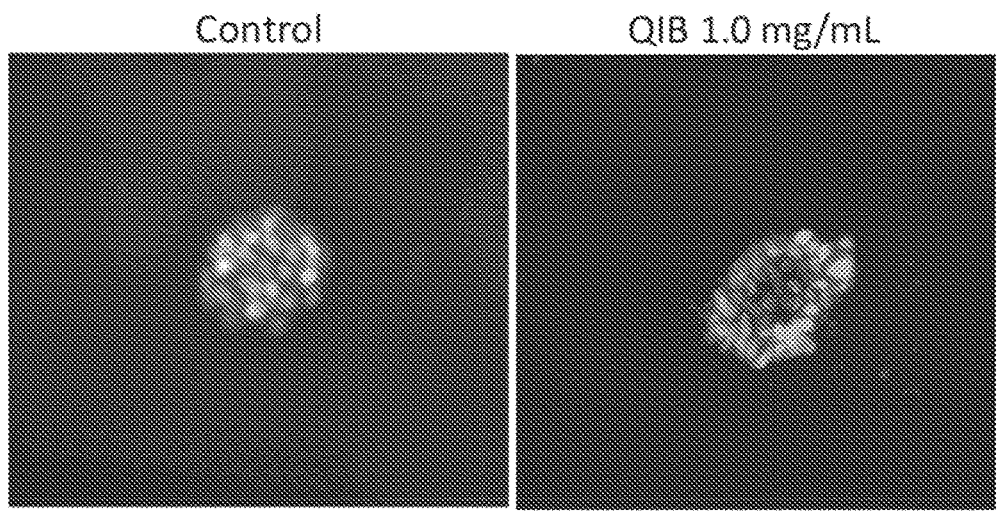
FIG. 7 shows representative images of day 1 dead cell staining of islet cells (4× magnification) exposed to control conditions (left) or amino acid formulation #2 (right) on day 1; blue staining shows the nucleus of all cells; overlaid red staining shows dead cells.

FIG. 7 illustrates examples of islets stained with live/dead fluorophores from day 1 comparing the control islets to those exposed to 1.0 mg/mL of Amino Acid Formulation #2 ("QIB"). Cells from the control group and the Amino Acid Formulation #2 (1.0 mg/mL) showed few dead cells on day 1.

Figure 8:
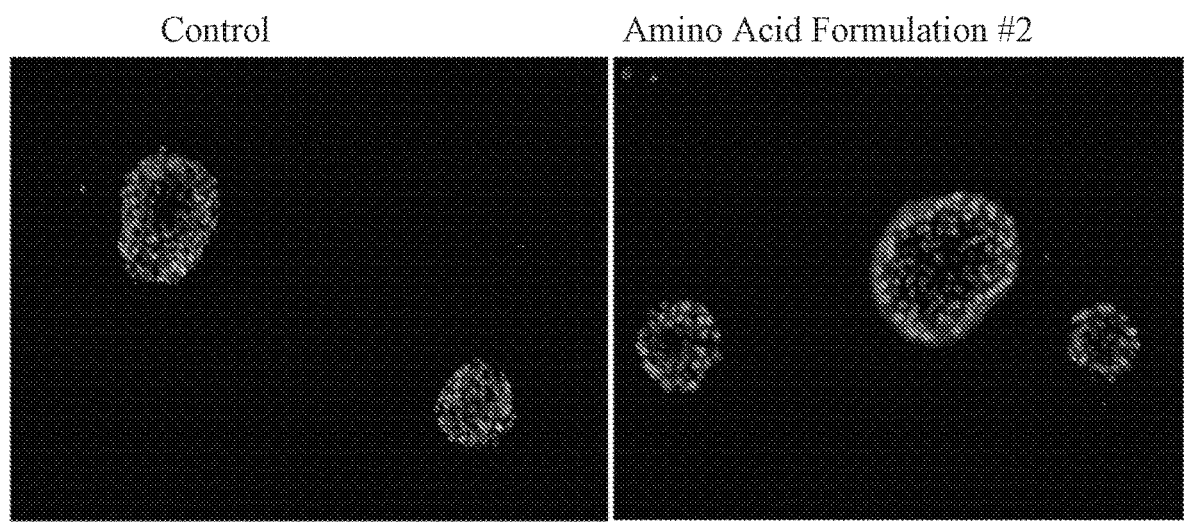
FIG. 8 shows representative images of day 4 viability of islet cells exposed to control conditions (left) or 1.0 mg/mL amino acid formulation #2 (right) on day 4; blue staining shows the nucleus of all cells; overlaid red staining shows dead cells.
Figure 9:
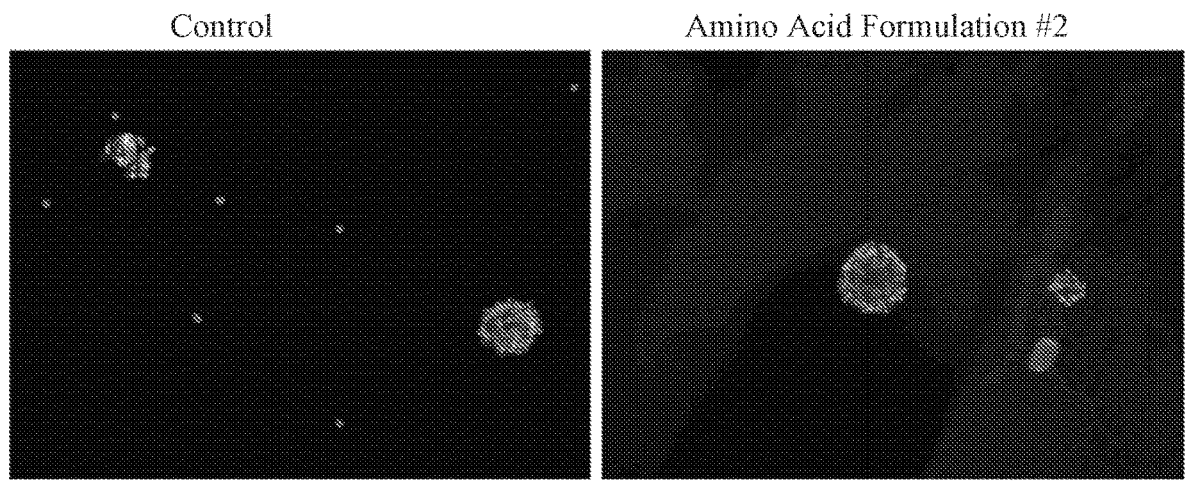
FIG. 9 shows representative images of day 8 viability of islet cells exposed to control conditions (left) or 1.0 mg/mL amino acid formulation #2 (right) on day 8; blue staining shows the nucleus of all cells; overlaid red staining shows dead cells.

There was not a clear difference in the number of dead cells per islet. The number of live and dead cells were manually counted for each islet and calculated as the percentage of live cells. The same measurements were taken on days 4 and 8. FIG. 8 illustrates examples of the islets on day 4 using 10× magnification, and FIG. 9 shows examples on day 8. Amino Acid Formulation #2 islets maintained their high viability rate (image on the right), while islets in the control group showed more cell death (red staining in image on the left).

Table 8 summarizes the findings for all 3 test dates by presenting the average viability value for each group±standard error. All islets identified in each condition were scored for the number of dead and live cells. The number of islets analyzed for each group varied due to the poor survival of islets in culture over time but ranged from 5-10/group.

TABLE 8

Viability Results

| Amino Acid Formulation #2 Concentration (mg/mL) | Time Point | Necrotic Cells (%) | Live Cells (%) |
|---|---|---|---|
| Control | Day 1 | 5.0 + 1.9 | 95.0 + 1.9 |
|  | Day 4 | 9.3 + 2.8 | 90.7 + 2.8 |
|  | Day 8 | 17.6 + 4.2 | 82.4 + 4.2 * |
| 0.25 | Day 1 | 1.9 + 0.7 | 98.1 + 0.7 |
|  | Day 4 | 10.6 + 3.9 | 89.4 + 3.9 |
|  | Day 8 | 5.3 + 1.9 | 94.7 + 1.9 |
| 0.50 | Day 1 | 0.0 + 0.0 | 100.0 + 0.0 |
|  | Day 4 | 5.4 + 1.9 | 94.6 + 1.9 |
|  | Day 8 | 3.7 + 0.8 | 96.3 + 0.8 |
| 1.00 | Day 1 | 0.5 + 0.5 | 99.5 + 0.5 |
|  | Day 4 | 4.6 + 0.9 | 95.4 + 0.9 |
|  | Day 8 | 0.9 + 0.5 | 99.1 + 0.5 |

* indicates a statistical difference from the other 3 groups, p = 0.001

There were no statistical differences found in the live cell percentages between the different concentrations of Amino Acid Formulation #2 and the control group on day 1 (p=0.095). Nor were there statistical differences between the groups on day 4 (p=0.230). However, on day 8, all three of the Amino Acid Formulation #2 groups had statistically greater numbers of live cells than the control values (p=0.001).

Figure 10:
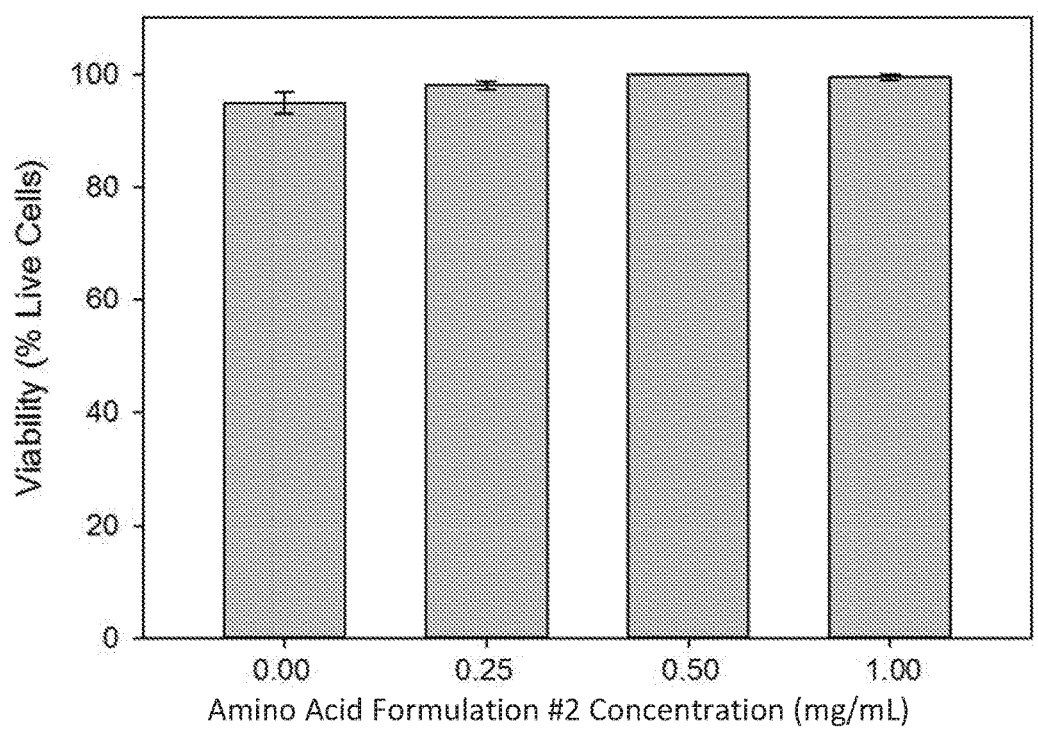
FIG. 10 shows a graph of the percentage of live islet cells calculated after a 24-hour exposure to Amino Acid Formulation #2.
Figure 11A:
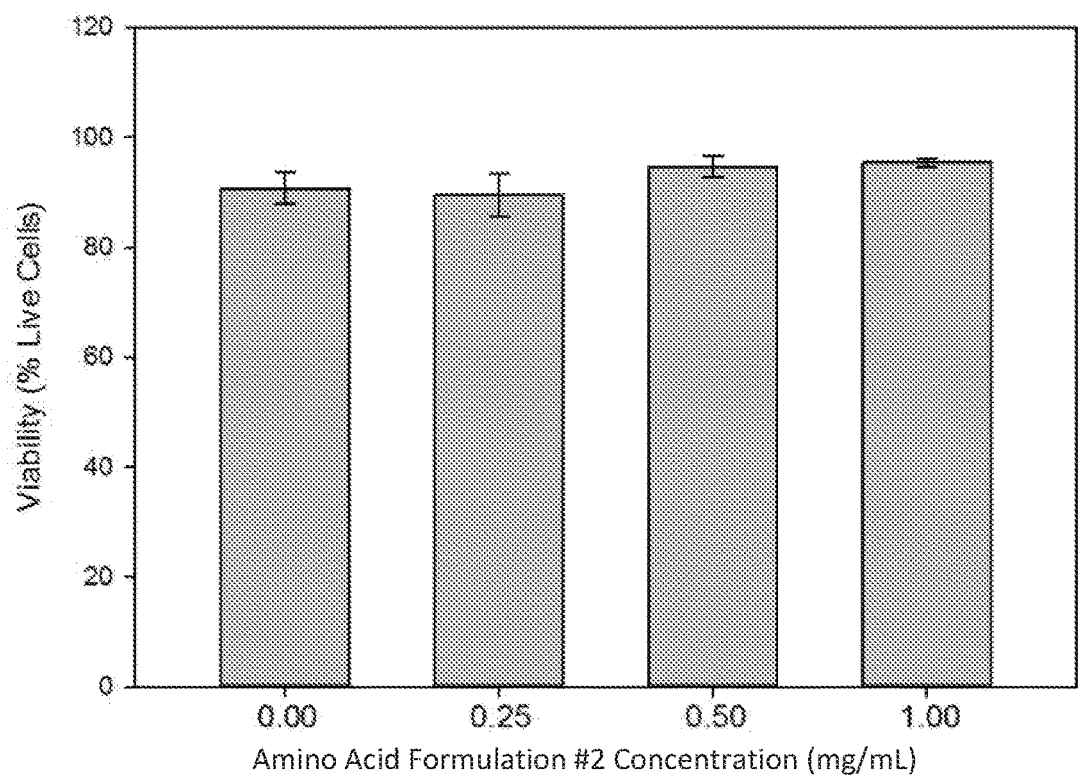
FIG. 11A is a graph of day 4 viability showing no difference between the groups.
Figure 11B:
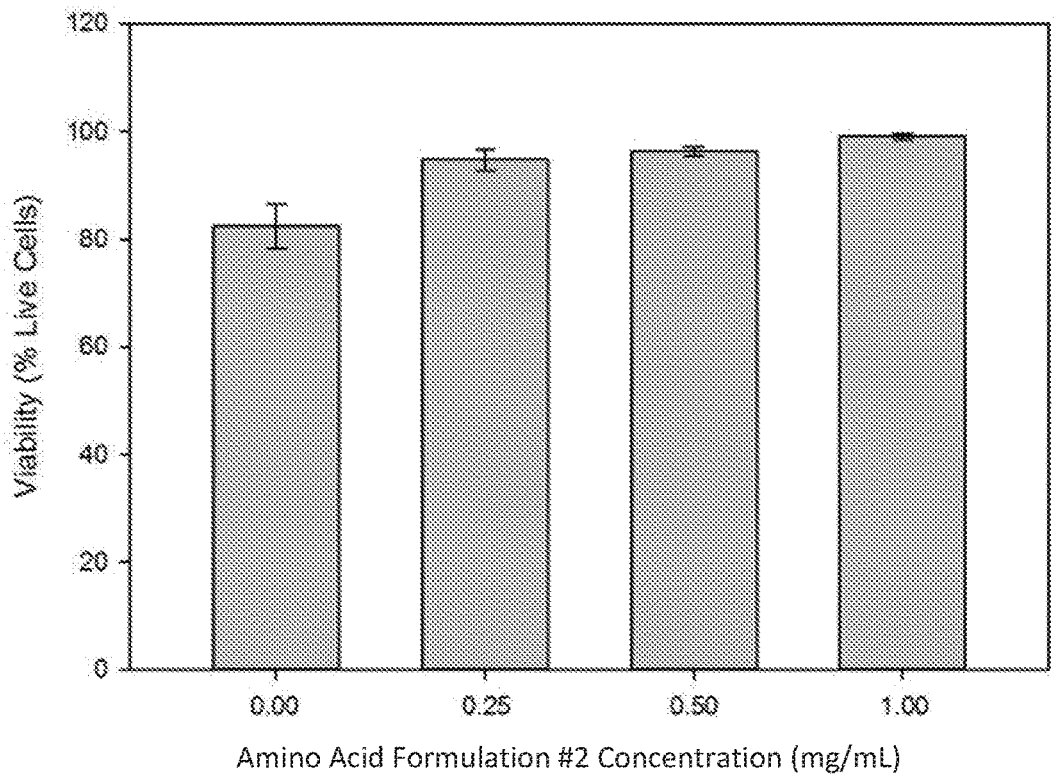
FIG. 11B is a graph of day 8 viability, and showing the viability in the control group had fallen to only about 80%.

Bar graphs shown in FIGS. 10 and 11 illustrate the point. On day 1 (FIG. 10) all of the cells within the islets were largely alive. In fact, in the islet group exposed to 0.50 mg/mL of Amino Acid Formulation #2, 100% of the cells in all the islets were alive on day 1.

By day 4 (FIG. 11A), there still were no differences in the viability percentages, and all islets were highly viable. However, by day 8 (FIG. 11B), one can clearly note the lower viability in the control group (zero exposure to the Amino Acid Formulation #2). The viability in the control group had fallen to nearly 80% viable. In contrast, islets incubated in any of the Amino Acid Formulation #2 concentrations maintained high viability levels.

3.1.3 Metabolism

Metabolism of cells indicates the health of the cell. The assay used here measures metabolism by accepting electrons from newly formed NDPH, FADH, NADH and cytochromes. The more electrons accepted, the greater the molecular fluorescence. Table 9 summarizes the raw data for the metabolism studies conducted on Day 8 of incubation with the test article, and the normalized data. Data were normalized by subtracting the background fluorescence (from the blank wells) and dividing by the number of islets per well. At 30 minutes, the metabolism of the islets in the Amino Acid Formulation #2 was 6 times greater than the control islets. When normalized for islet numbers and background signal, the islets incubated in the Amino Acid Formulation #2 continued to demonstrate higher metabolism.

TABLE 9

Metabolism Results

| | Raw Data | | | | Normalized Data (normalized to islet number) | | | |
|---|---|---|---|---|---|---|---|---|
| | 30 min | 1 hour | 3 hour | 7 hour | 30 min | 1 hour | 3 hour | 7 hour |
| Blank | 7 | 14 | 3 | 11 | na | na | na | na |
| Plate 2 | 9 | 9 | 11 | 8 | | | | |
| | 12 | 65 | 62 | 57 | | | | |
| | 10 | 10 | 9 | 12 | | | | |
| QIB#2* | 8034 | 8757 | 9796 | 10648 | 1003 | 1092 | 1222 | 1328 |
| 1.0 | 6058 | 7179 | 8316 | 9908 | 864 | 1022 | 1185 | 1412 |
| mg/mL | 4693 | 5411 | 6113 | 7414 | 937 | 1077 | 1218 | 1478 |
| QIB#2 | 8553 | 8784 | 9094 | 9309 | 1220 | 1253 | 1298 | 1327 |
| 0.5 | 1498 | 2259 | 2533 | 2992 | 743 | 1124 | 1263 | 1487 |
| mg/mL | 8260 | 8638 | 8633 | 8855 | 1178 | 1232 | 1232. | 1262 |
| | 8162 | 8623 | 8577 | 8729 | 1164 | 1230 | 1224 | 1244 |
| QIB#2 | 8702 | 8802 | 8739 | 9048 | 1242 | 1245 | 1245 | 1290 |
| 0.25 | 10339 | 10757 | 10991 | 12032 | 1148 | 1191 | 1219 | 1335 |
| mg/mL | 10824 | 11269 | 11340 | 12020 | 1202 | 1249 | 1258 | 1333 |
| | 5881 | 5921 | 6251 | 6544 | 1174 | 1179 | 1246 | 1305 |
| Control | 6095 | 6413 | 6534 | 6728 | 1217 | 1280 | 1305 | 1342 |
| | 6819 | 6746 | 6948 | 7467 | 1362 | 1347 | 1388 | 1490 |
| | 6742 | 7251 | 7451 | 7681 | 1346 | 1448 | 1489 | 1532 |
| | 11223 | 11313 | 10740 | 10976 | 1246 | 1256 | 1192 | 1217 |

*QIB#2 refers to Amino Acid Formulation #2.

Figure 12:
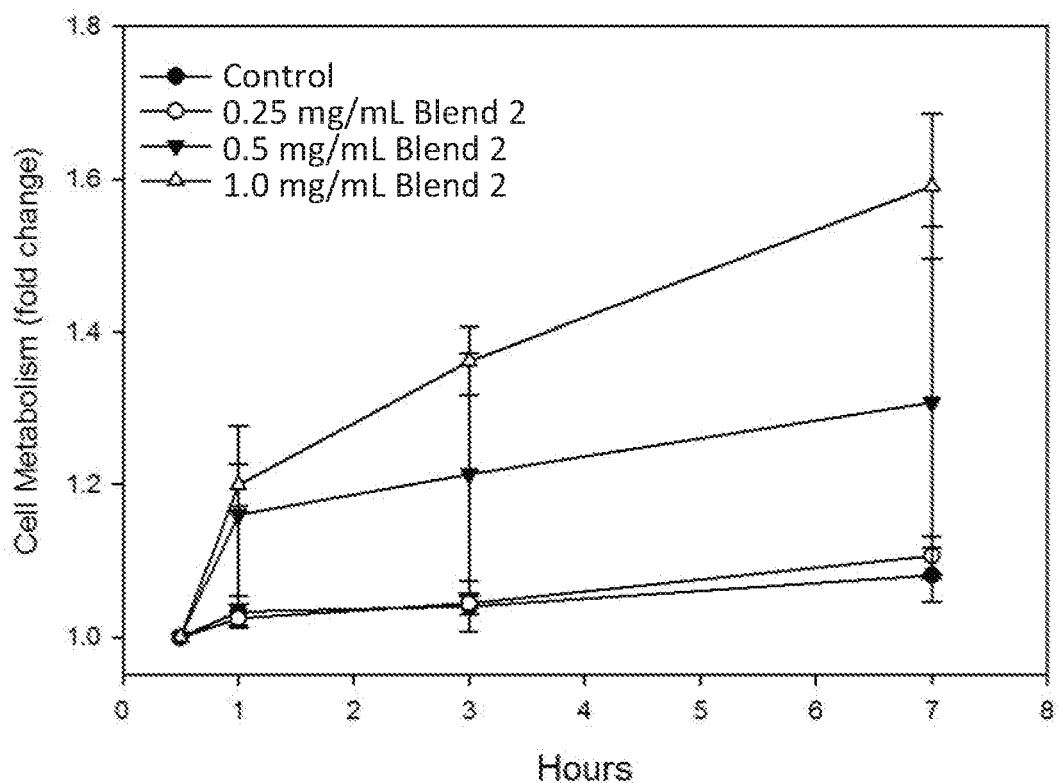
FIG. 12 is a graph of cell metabolism comparison between various concentrations of amino acid formulation #2 and the control cells.

The data show an increase in metabolism over time in all 4 groups. However, the average percent increase was greatest in the groups that were incubated in the Amino Acid Formulation #2. FIG. 12 illustrates this point by normalizing the raw data, not to the number of islets, but simply to the percent change in metabolic fluorophore.

30 minutes after the addition of the metabolism detector, the first measurement was taken, and all data were normalized to the initial values for each group. At 1 hour, the metabolic level was greater in the islets from the Amino Acid Formulation #2 group at the 2 highest concentrations (open and closed triangles). This trend continued through the duration of the study.

In FIG. 12, there is a slight increase in metabolic fluorophore emission over time in the control group. However, at 3 hours of incubation, the dose/response of the Amino Acid Formulation #2 can be identified, with the highest metabolism in the 1.0 mg/mL group and the next highest level in the 0.5 mg/mL group, with the 0.25 mg/mL and the control groups indistinguishable. By hour 7, there was greater separation of the values obtained by the 3 concentrations of Amino Acid Formulation #2, illustrating the dose-sensitivity. However, the values at 7 hours were not statistically different.

Figure 13:
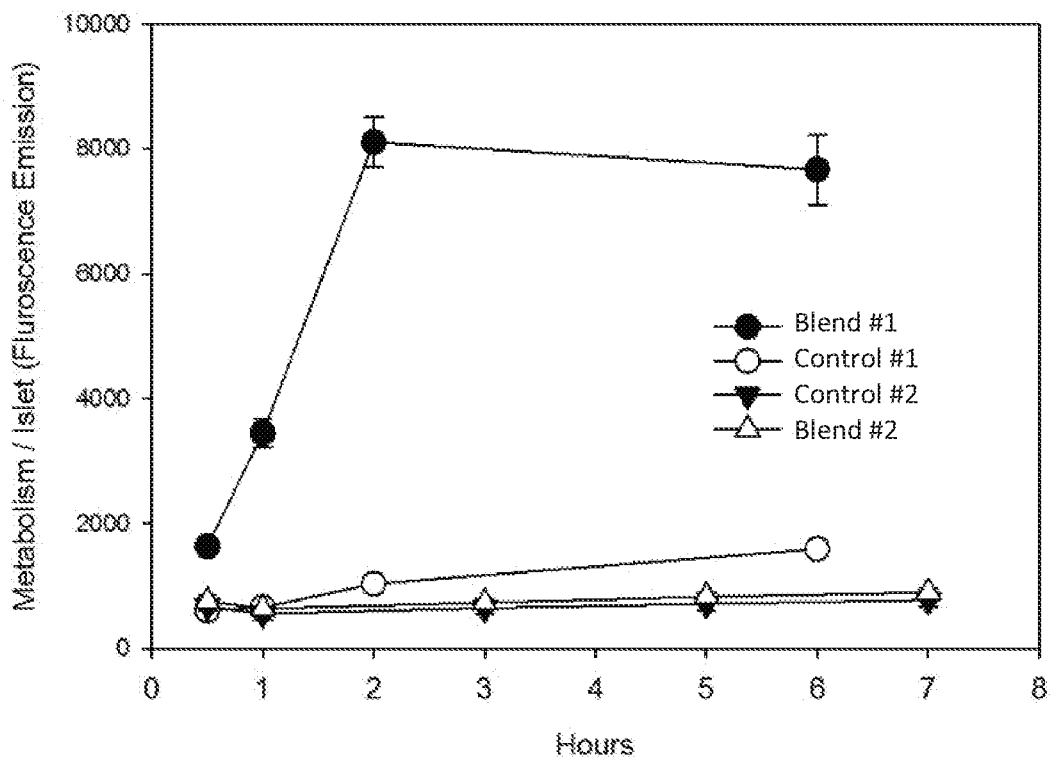
FIG. 13 is a graph of the comparison of amino acid blends 1 and 2 against control in rat islets.

The metabolic test was repeated in rat islets. FIG. 13 summarizes the results of Amino Acid Formulation #1 and Amino Acid Formulation #2 compared in rat islets. Metabolism/islet was significantly higher in the rat islets with Amino Acid Formulation #1 than with Amino Acid Formulation #2.

3.2 Summary of Data

Islet cells are difficult to maintain in culture. They do not proliferate and are not self-renewing. In fact, they are one of the most sensitive cells to inflammation in the body. For this study, islets were cultured in a high glucose environment to further stress the cells and to simulate a diabetic condition. Furthermore, canine diabetes is nearly identical to human type 1 diabetes, and thus canine islets are an excellent model for testing the effects of any drug or test article on islet health.

Islets were stained at days 1, 4, and 8 for viability by measuring cells undergoing necrotic cell death. First the nuclei of all cells were stained, and then dead cells were counterstained. Cells exposed to the Amino Acid Formulation #2 had the highest viability at the final time point (day 8), which was statistically greater than the control values.

Metabolism of cells indicates their general health and activity. Metabolism of the islets in each group was measured on day 8. 30 minutes after the addition of the electron detector, the metabolism of the islets in the Amino Acid Formulation #2 group was higher than the controls and this trend continued through the 7-hour study. The data were normalized both to the number of islets in each well and to the percent change over time. With both normalization procedures, the islets in the Amino Acid Formulation #2 group were still more metabolically active.

Example 3

1. Introduction

The objective of the non-GLP studies described here was to test the effect of exposure of cultured beta cells to a variety of single amino acids, followed by amino acids combined as doublets and compare the results to the therapeutic blends of the amino acids. Cellular metabolism was the outcome measure as an indication of overall cell health and the number of viable cells.

The therapeutic blends show an enhancement of cell metabolism far about individual or double amino acid blends. At low doses, all three therapeutic blends tested showed an enhancement of metabolism over controls. Blend A had the greatest increase in metabolism values at concentrations between 0.1 to 1.0 mgs, but showed signs of toxicity at the highest concentration of 5 mg/mL. Blends B and C continued to have improved responses with the greatest response at the highest concentration.

2. Materials and Methods

The Humanized cultured beta-cells (INS-1 832/13) a derivation of the INS-1 cell line, were cultured in a growth medium consisting of RPMI-1640, along with 1 M HEPES buffer solution, 50×INS supplement (glutamine, Na-pyruvate, and B-mercaptoethanol), Antibiotic-Antimycotic (Gibco by LifeTechnologies), and Fetal Bovine Serum (HyClone). Cells were grown and sustained in a T75 cell culture flask. The cells were placed in a humidified incubator at 37° C. and 5% CO2. Due to the rapid growth of these cells, media was changed on every second day and passaged on every fourth day via trypsinization. When cells were confluent, they were exposed to amino acids as described below.

The tested amino acids, manufactured by JoMar Labs, were blended according to the list below.

TABLE 10

Summary of Stock Blends

| Blend | Component | Weight (g) |
| --- | --- | --- |
| Blend A | L-Serine | 39.67 |
| | Glutamic Acid | 40.13 |
| | L-Threonine | 39.63 |
| | L-Cysteine | 39.54 |
| | L-Asparagine | 40.02 |
| Blend B | L-Serine | 36.64 |
| | Glutamic Acid | 39.58 |
| | L-Threonine | 39.97 |
| | L-Lysine | 39.89 |
| | L-Isoleucine | 39.75 |
| Blend C | L-Serine | 39.56 |
| | Glutamic Acid | 39.78 |
| | L-Isoleucine | 39.84 |
| | L-Lysine | 39.57 |
| | Carnitine | 39.63 |

2.1 Sample Preparation and Assay

For the full study, cells plated in 384-well plates were exposed to individual amino acids at 10 full-log doses for 4 hours at 37° C. and 5% $CO_2$. PrestoBlue (10%) was added to each well using the Hamilton Star Automated Fluid Handling System, and 1 hour later, for a total of 5 hours of exposure to the amino acids.

The plates were loaded into the EnSpire plate reader with excitation of 560 nm and emission of 590 nm excitation wavelengths. For blends, additional kinematic studies were undertaken. Additional kinematic studies were conducted for the following 5 hours. Raw data were saved as Excel spreadsheets.

Control wells of cells exposed to glycine only were included in every plate reading.

3. Results 3.1 Data & Analysis

Figure 14A:
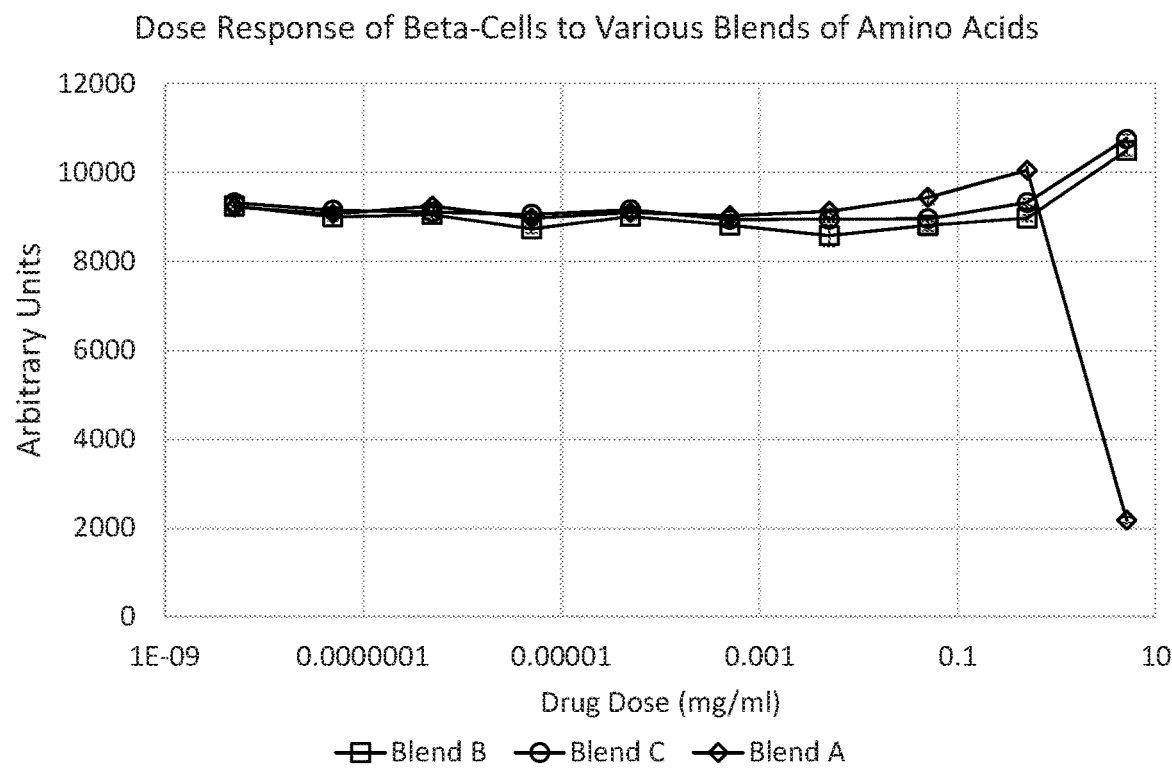
FIG. 14A is a graph of the raw data of the dose response of cells to the three blends tested in Example 3.
Figure 14B:
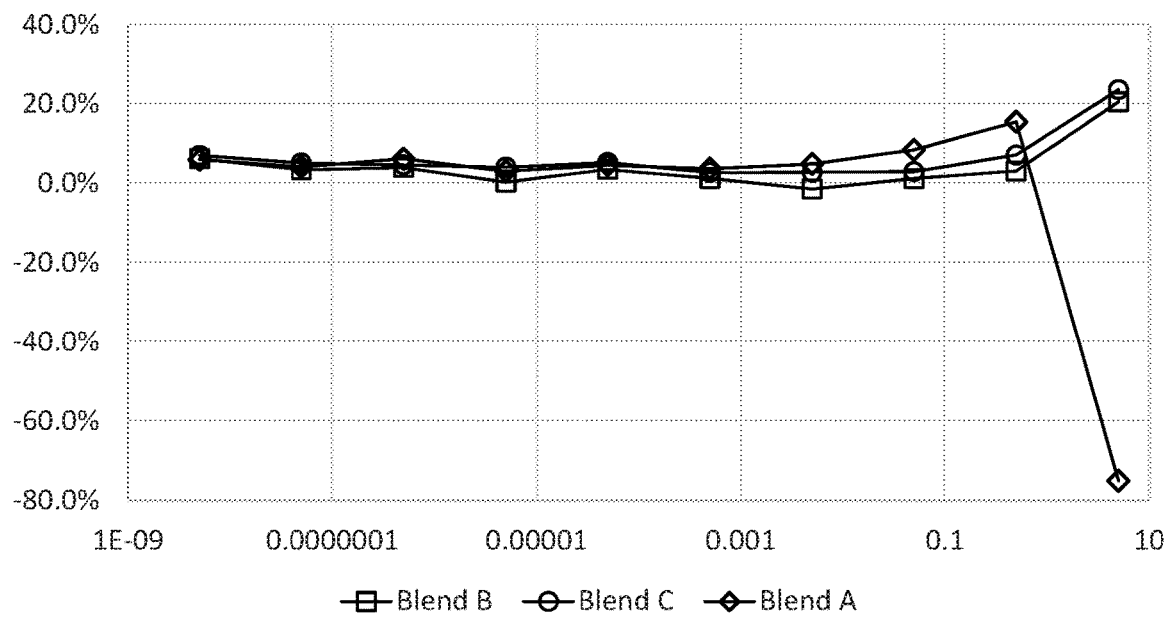
FIG. 14B is a graph of the normalized data of the dose response of cells to the three blends tested in Example 3, as a percentage response in comparison to non-treated (control) cells.

The results are shown in FIGS. 14A and 14B. The test of the blends is shown both as the background-subtracted data and as data normalized to the control wells. In the second plot, the 0% line indicates the response of the control cells.

3.2 Summary of Data

In this study, the effect of the therapeutic blends can be seen to be above control cells for almost every concentration tested. All cells responded to the amino acids in a favorable manner at low doses. However, once concentrations above 1 mg/mL were reached, there was a sharp contrast in the responses. Cells exposed to the Blend A showed signs of toxicity, while those exposed to Blend B and C showed improved viability and metabolism.

Example 4

1. Introduction

The objective of these experiments was to test the effect of single amino acids on the viability of a human beta-cell culture line, followed by examination of synergistic effects by crossing all 10 amino acids.

While most of the single amino acids had no effect on cell viability, cysteine was found to improve viability at the higher concentrations tested. In contrast arginine and asparagine had negative effects on cell viability at the highest doses. When crossing the amino acids in duplicates, unexpected relationships were uncovered.

2. Materials and Methods

The human beta-cell line (INS-1 832/13) was expanded and maintained in RPMI-1640 growth media during expansion. Cells were grown and sustained in T75 cell culture flasks in an incubator at 37° C. and 5% $CO_2$. Cells were passaged every 4th day via trypsinization. All cell media changes and passage work was done under a biosafety hood to ensure sterility of the cultures. Readings were obtained from the EnSpire Multimode Plate Reader (Perkin Elmer) with excitation of 560 nm and emission of 590 nm. To avoid plate edge effects the outer wells of each plate were used as blanks.

2.1 Sample Preparation

The INS-1 832/13 cell line, a derivation of the INS-1 cell line, was cultured in a growth medium consisting of RPMI-1640, along with 1 M HEPES buffer solution, 50×INS supplement (glutamine, Na-pyruvate, and B-mercaptoethanol), Antibiotic-Antimycotic (Gibco by LifeTechnologies), and Fetal Bovine Serum (HyClone). Cells were grown and sustained in a T75 cell culture flask. The cells were placed in a humidified incubator at 37° C. and 5% CO2. Due to the rapid growth of these cells, media was changed on every second day and passaged on every fourth day via trypsinization. When cells were confluent, they were exposed to amino acids as described below.

Amino acids, manufactured by JoMar Labs, are listed below. Amino acid combinations were tested in 1:1 weight ratios.

2.2 Viability Assay

Pilot studies were undertaken with 6 single amino acids to determine the optimal conditions for cell testing, and the optimal time for exposure to the amino acids. Cells in media with the test amino acids failed to show any effect, even after a 24-hour exposure. Thus, a second trial was undertaken removing the media and placing cells in phosphate buffered saline at the time of the amino acid addition. After 4 hours, some of the wells showed negative effects (cell death) at the highest concentrations. Thus, the optimal conditions were determined to be a 5-hour exposure to the amino acids in PBS.

For the full study, cells plated in 384-well plates were exposed to individual amino acids at 10 full-log doses for 4 hours at 37° C. and 5% CO2. PrestoBlue (10%) was added to each well using the Hamilton Star Automated Fluid Handling System, and 1 hour later, for a total of 5 hours of exposure to the amino acids.

The plates were loaded into the EnSpire plate reader with excitation of 560 nm and emission of 590 nm excitation wavelengths. Raw data were saved as Excel spreadsheets.

3. Results

Figure 15:
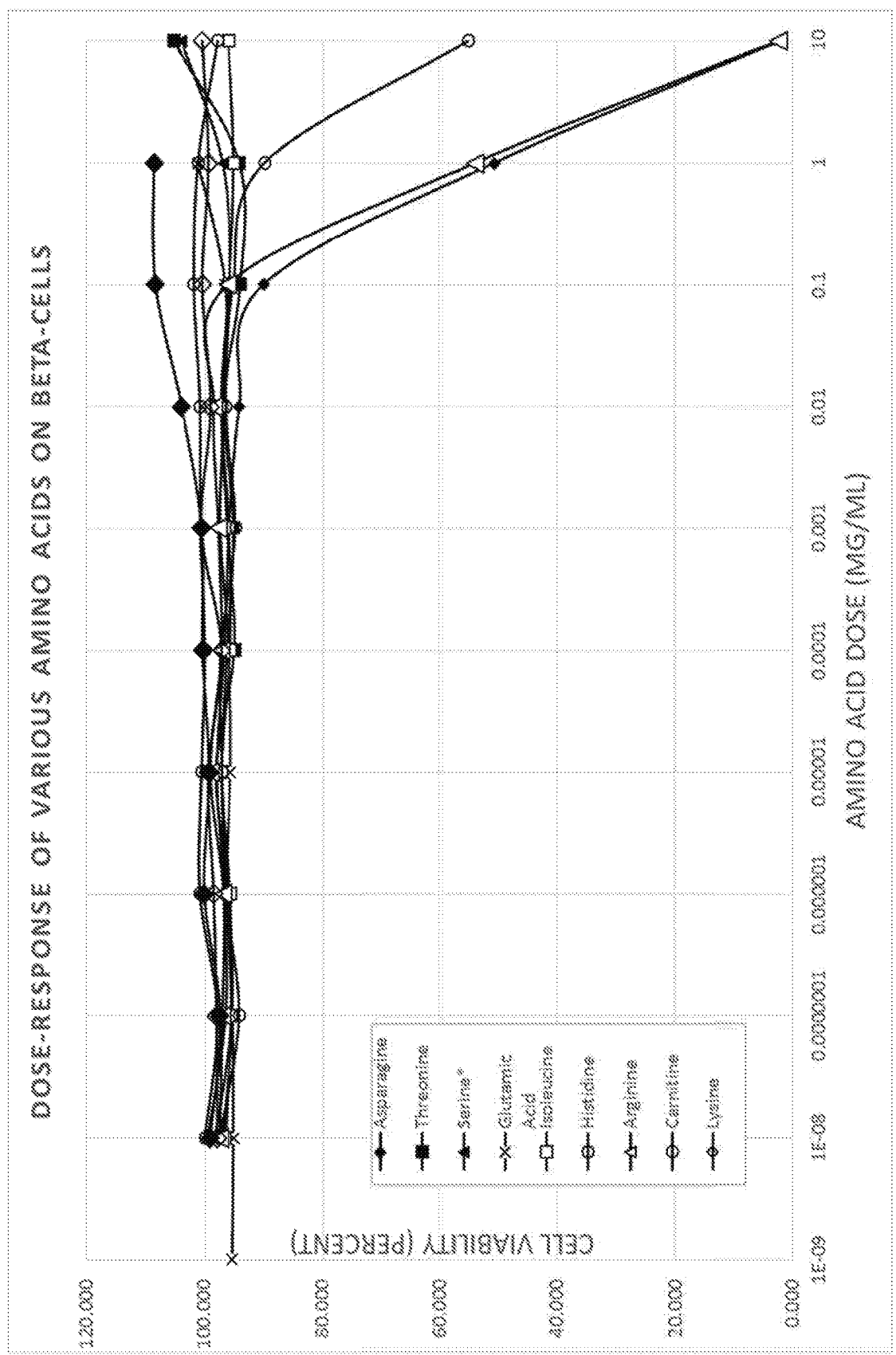
FIG. 15 is a graph of the dose response of islet beta cells to different individual amino acids.

The results of the effect of single amino acids to beta-cell health is shown in FIG. 15. Amino acids were added to a minimal buffer in full log concentrations starting at 1E−08 through 10 mg/mL. The only exception was glutamic acid, which would not go into solution at 10 mg/mL, and thus the range of doses tested was reduced. Cysteine is known to be a strong reducing agent and interfered with the viability assay at concentrations above 1 mg/mL. In the graph, the data have been normalized to cell viability in minimal buffer with no amino acids (100%).

At low doses the single amino acids had no effect on beta cell health. At 0.01 mg/mL and higher, cysteine had a positive impact on cell viability. At 10 mg/mL threonine and serine had slightly positive increases in viability. In contrast, starting at 1 mg/mL asparagine, arginine and histidine showed dramatic reductions in the viability of the beta cells, with arginine and asparagine killing nearly 1000% of the cells and histidine killing approximately half of the cells.

Figures 16, 17:
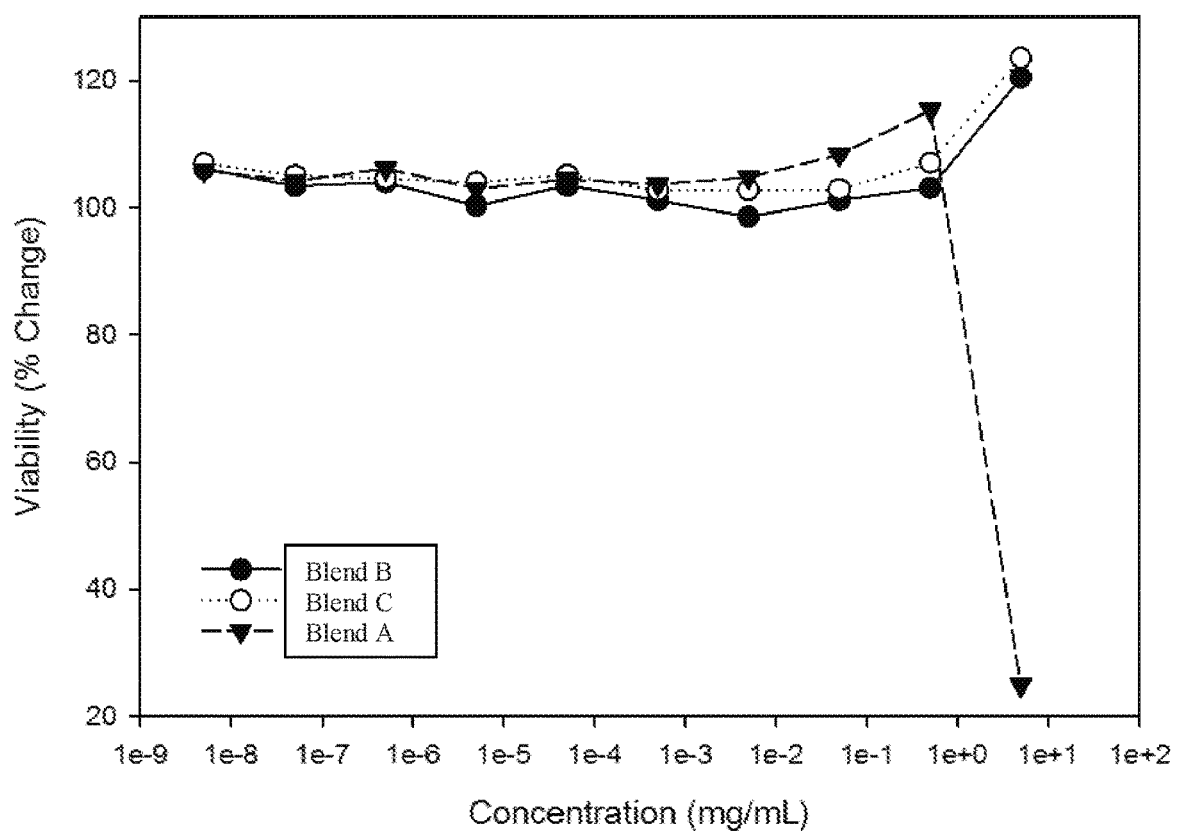
FIG. 16 is graph showing the normalized data of crosses with 2 amino acids.
FIG. 17 is a graph showing the percent change in viability in islet cells exposed to different amino acid blends in Example 4 at various dosages.

The normalized data of crosses with 2 amino acids is presented in FIG. 16. Shades of red (18%, 20%, 16%, 32%) indicate an antagonistic interaction. Blue indicates no adverse interaction, while dark blue (114%) indicates a synergistic interaction.

Double Crosses of Amino Acids

When these same amino acids were crossed into blends that contained each combination of 2 amino acids, the results were in line with the results from the single amino acid testing. Each amino acid was added to the cell buffer at a concentration of 1 mg/mL. The top line of the chart shows the single amino acid results repeated. Again, asparagine shows a dramatic reduction in beta cell viability at a concentration of 1 mg/mL. When the double crosses were made, the addition of another 1 mg/mL of asparagine to asparagine, resulted in only 18% of the cells left in the dish that were alive. More importantly, any addition of asparagine to any other amino acid, except cysteine, resulted in significant cell death. Likewise, arginine showed a decrease in cell viability when added to any other amino acid. Histidine, on the other hand, had very little effect on cell viability except when paired with asparagine or arginine. These results are consistent with those of the single amino acid testing shown in the graphs.

Cysteine showed some interesting findings. As shown in the graph, cysteine alone had the most positive effect on cell health. However, when blended with glutamic acid, isoleucine, or lysine there was a dramatic loss of cell viability in the range of 30-40% cell. Yet cysteine with arginine, asparagine or histidine, appeared to blunt the negative response of those 3 individual amino acids.

Inventive Blends

The graph in FIG. 17 summarizes the results of the dose/response testing. The X axis shows the concentration of each blend so that the results can be directly compared to the double combinations. Thus, a concentration of 1 mg/mL of a single amino acid is actually a 5 mg/mL of the full blend, because there are 5 different amino acids in each blend mixed in equal amounts.

At low concentrations there was a modest synergistic effect of all 3 blends. The improved viability was greater than any of the amino acids alone at the same concentration, with the exception of cysteine. At 0.5 mg/mL, all 3 blends started to show some improvement in cell viability, with Blend A demonstrating the greatest effect. However, at 5 mg/mL, Blend A induced a severe decline in viability with fewer than 25% of the cells left alive. In contrast, Blends B and C improved cell viability significantly with nearly a 20% improvement in cell viability. When measuring a culture cell line, it is challenging to find components that will improve viability.

In summary, all cells responded to the amino acids in a favorable manner at low doses. However, once concentrations above 1 mg/mL were reached, there was a sharp contrast in the responses. Cells exposed to Blend A showed signs of toxicity at higher concentrations, while those exposed to Blend B and C continued to show improved viability and metabolism.

Example 5

Pilot Case Studies

In the following pilot case studies, subjects were orally administered a 520-mg amino acid formulation in capsule form twice per day (morning and night). Each capsule contained L-lysine (120 mg, HCl salt form), L-isoleucine (100 mg), L-threonine (100 mg), L-serine (100 mg), and glutamic acid (100 mg).

1. Subject: T
   Age: 58
   Sex: F
   Health Status: Diagnosed with Type 2 Diabetes for over 4 years. Subject has been using Metformin for past 4 years and during the duration of study, her dosage of Metformin has remained unchanged. Initial blood glucose level of over 310+ mg/dL.
   Over the course of seven weeks, daily monitoring of glucose levels showed a rapid decrease in the blood glucose levels by over 90 mg/dL when taking the formulation.

2. Subject: JH
   Age: 26
   Sex: F
   Health Status: Type 1 Diabetes, uses insulin supplementation to manage insulin levels. Prior to beginning study, Subject reported experiencing wide fluctuations in insulin intake. Subject uses Dexcom, an autocalibration and automated insulin delivery system which monitor's glucose levels continuously. Subject measures A1C levels 4× per year as part of routine medical care for Type 1 Diabetes to determine how well the diabetes management plan is working. The A1C test measures the glucose (blood sugar) in the blood by assessing the amount of glycated hemoglobin. At the beginning of the study, Subject had an A1C level of 8.5, and reported that she had experienced a continuous increase in her A1C levels over the past several years. After 45 days of supplementation with the amino acid formulation, the Subject's A1C level had decreased to 7.5.

3. Patient: ES
   Age: 26
   Sex: F
   Health Status: Type 1 Diabetes, uses insulin supplementation to manage insulin levels. Prior to beginning study, Subject reported experiencing wide fluctuations in insulin intake. Subject uses Dexcom, an autocalibration and automated insulin delivery system which monitor's glucose levels continuously. Prior to beginning the study, the Subject's Insulin report indicated that the Subject had average glucose levels of 152 mg/dl and had a percentage of time in the normal insulin range of 62% and a 35% time above the normal range. After 21 days of supplementation with the amino acid formulation, the Subject's average glucose level decreased to 146 mg/dl, time in normal insulin range increased to 66%, and time above the normal range decreased to 31%.

4. Patient: DM
   Age: 28
   Sex: F
   Health Status: Prediabetic, doesn't use insulin supplementation or any other medication. Pre-diabetics often always have slower fat metabolism due to insulin resistance and seldom lose weight. Subject participated in a 21-day pilot study focused on fat metabolism and weight loss. Subject's initial weight was measured at 206 pounds. After the 21-day study, subject reported a weight loss of 6 pounds.

5. Patient: MF
   Age: 55
   Sex: F
   Health Status: Prediabetic, doesn't use insulin supplementation or any other medication. Subject participated in the 21-day pilot study focused on fat metabolism and weight loss. Subject's initial weight was measured at 204 pounds and after the completion of the 21-day study, subject reported a weight loss of 1-2 pounds.

6. Patient: RS
   Age: 50
   Sex: M
   Health Status: Type 2 Diabetes, has been diagnosed with Type 2 Diabetes for over 10 years. Subject initially started with an average blood glucose level of over 310+ mg/mL and daily monitoring of glucose levels showed a rapid decrease in the blood glucose levels by over 100 mg/mL after 2 weeks of supplementation. Subject also reported a change in BMI and degrease in glycemic levels.

The invention claimed is:

1. A method of enhancing pancreatic vitality in a subject in need thereof, said method comprising administering a therapeutically effective amount of a synergistic amino acid formulation consisting essentially of a mixture of glutamic acid, isoleucine, lysine, serine, and threonine to the subject, to thereby enhance the pancreatic vitality of the subject.

2. The method of claim 1, wherein said amino acid formulation is administered to the subject in need thereof for a therapeutically effective amount of time.

3. The method of claim 1, wherein said mixture comprises said amino acids blended together in unit dosage form.

4. The method of claim 3, wherein said unit dosage form comprises from about 400 to about 600 mg of said mixture.

5. The method of claim 4, wherein said unit dosage form is a pill, tablet, capsule, or gel cap containing said mixture.

6. The method of claim 1, wherein said mixture is substantially free of one or more amino acids selected from the group consisting of: alanine, aspartic acid, glutamine, glycine, leucine, methionine, phenylalanine, proline, tryptophan, tyrosine, and valine.

7. The method of claim 1, wherein said mixture is substantially free of cysteine and asparagine.

8. The method of claim 1, wherein said mixture is substantially free of arginine and histidine.

9. The method of claim 1, wherein the subject is a diabetic subject having elevated blood glucose levels, said method comprising administering a therapeutically effective amount of the amino acid formulation to said subject for a therapeutically effective amount of time to thereby decrease or stabilize the blood glucose levels in said subject.

10. The method of claim 9, wherein said amino acid formulation is administered daily, twice per day as a unit dosage form.

11. The method of claim 9, wherein A1C levels in the diabetic subject are decreased or stabilized after administering the therapeutically effective amount of the amino acid formulation to said subject for a therapeutically effective amount of time.

* * * * *